United States Patent
Rostrup-Nielsen et al.

(10) Patent No.: US 7,910,630 B2
(45) Date of Patent: Mar. 22, 2011

(54) PROCESS FOR THE PREPARATION OF PURE DIMETHYL ETHER

(75) Inventors: Thomas Rostrup-Nielsen, Holte (DK); Jørgen Madsen, Hillerød (DK)

(73) Assignee: Haldor Topsøe A/S, Lyngby (DK)

( * ) Notice: Subject to any disclaimer, the term of this patent is extended or adjusted under 35 U.S.C. 154(b) by 219 days.

(21) Appl. No.: 12/272,910

(22) Filed: Nov. 18, 2008

(65) Prior Publication Data
US 2009/0156698 A1 Jun. 18, 2009

(30) Foreign Application Priority Data
Dec. 13, 2007 (DK) .................. 2007 01777

(51) Int. Cl.
*C07C 27/00* (2006.01)
(52) U.S. Cl. .............. 518/706; 518/700; 518/705
(58) Field of Classification Search ........... 518/700, 518/705, 706
See application file for complete search history.

(56) References Cited

U.S. PATENT DOCUMENTS
5,908,963 A 6/1999 Voss et al.
6,458,856 B1 10/2002 Peng et al.

FOREIGN PATENT DOCUMENTS
GB 1102943 2/1968

OTHER PUBLICATIONS

Greene et al., carbon dioxide removal and recovery—new polyglocol ether processes, (Proceedings of the gas conditionings conference (1995) 1H-21H.*
Hernandez et al., solvent unit cleans synthesis gas, (chemical engineering (New York, NY, United States) (1989), 62 (2), 154-156.*

* cited by examiner

*Primary Examiner* — Jafar Parsa
(74) *Attorney, Agent, or Firm* — Dickstein Shapiro LLP

(57) ABSTRACT

Process for the preparation of dimethyl ether product by catalytic conversion of synthesis gas to dimethyl ether comprising the steps of contacting a stream of synthesis gas comprising carbon dioxide in a dimethyl ether synthesis step in one or more reactors and with one or more catalysts being active in formation of methanol and dehydration of methanol to dimethyl ether, to form a product mixture comprising the dimethyl ether and carbon dioxide, washing the product mixture in a scrubbing zone with a liquid solvent being rich in dialkyl ether of a polyalkylene glycol and thereby dissolving carbon dioxide and dimethyl ether in the liquid solvent, treating the liquid solvent being withdrawn from the scrubbing zone sequentially in separation zone to effect desorption of the dissolved carbon dioxide and to recover a substantially pure dimethyl ether product and the liquid solvent in its substantially lean form and recycling the lean liquid solvent to the scrubbing zone.

8 Claims, 1 Drawing Sheet

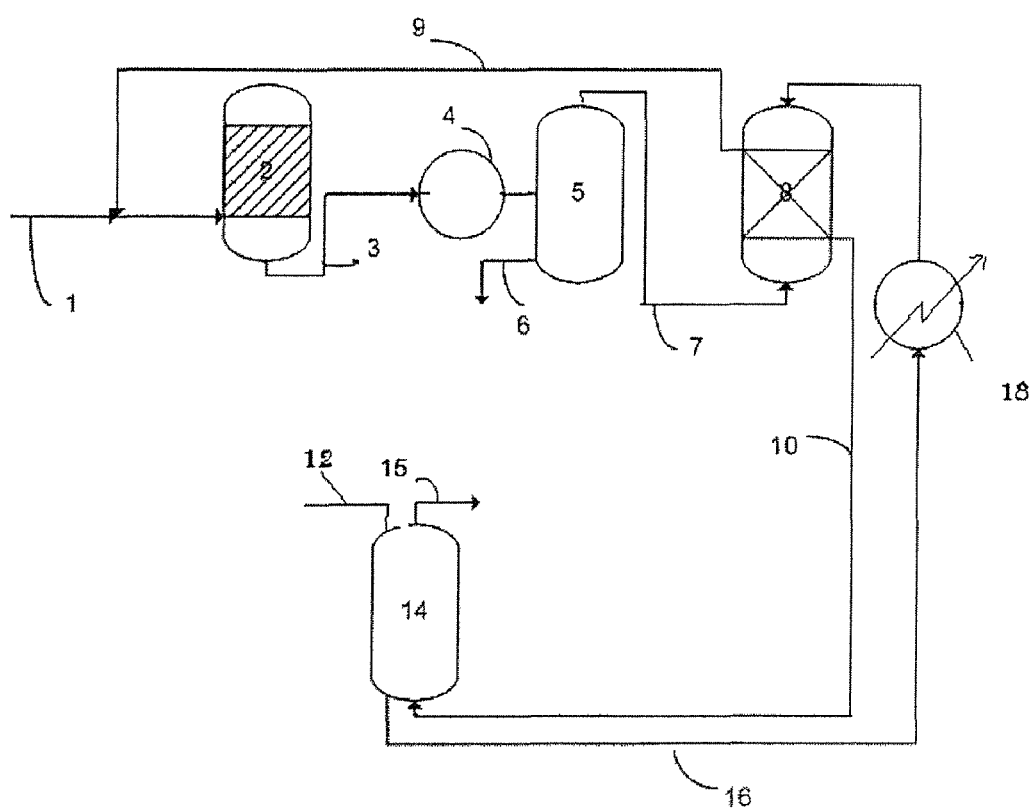

PROCESS FOR THE PREPARATION OF PURE DIMETHYL ETHER

The invention concerns a process for preparation of dimethyl ether from synthesis gas. In particular, the invention concerns an improved dimethyl ether synthesis process by utilising physical wash of raw product effluent from the ether synthesis step for the removal of carbon dioxide from the raw product to improve process yield and the final purification of produced dimethyl ether.

BACKGROUND OF THE INVENTION

The process of the invention concerns purification of dimethyl ether being produced from carbon oxides and hydrogen containing synthesis gas.

The conversion of synthesis gas to dimethyl ether is carried out in one or more reactors, in which synthesis gas is catalytically converted to methanol shown in equation (1), and dimethyl ether as shown in equation (2). The shift reaction also takes place and is shown in equation (3).

$$CO + 2H_2 \rightarrow CH_3OH \quad (1)$$

$$2CH_3OH \rightarrow CH_3OCH_3 + H_2O \quad (2)$$

$$CO + H_2O \rightarrow CO_2 + H_2 \quad (3)$$

Maximum conversion of synthesis gas is obtained when dimethyl ether is prepared at a stoichiometric ratio between hydrogen and carbon monoxide equal to one. At ratios above or below one less dimethyl ether is prepared. At maximum conversion ($H_2/CO \approx 1$) the overall reaction takes place essentially according to equation (4):

$$3H_2 + 3CO \rightarrow CH_3OCH_3 + CO_2 \quad (4)$$

Carbon dioxide is soluble in dimethyl ether and in order to obtain the dimethyl ether product with a required purity, it is necessary to remove the carbon dioxide formed. Additionally, when carbon dioxide is removed the composition of the unconverted synthesis gas, which is recycled to the dimethyl ether synthesis reactor, is close to that of the make up synthesis gas used to prepare dimethyl ether, which is an additional advantage. Removal of carbon dioxide from the dimethyl ether product downstream the synthesis reactor can become very costly.

Three basic processes for disposing off carbon dioxide are known. In the first process dimethyl ether is synthesized according to reactions (1) to (3) above. A mixed effluent stream comprising unreacted synthesis gas together with any carbon dioxide present is then separated from the dimethyl ether product which also contains some unreacted methanol. The separated synthesis gas and carbon dioxide stream are recycled to the synthesis gas process stream entering the reactor. This process may conveniently be applied in a hydrogen rich synthesis gas having for instance a ratio between hydrogen and carbon monoxide above 5.

In the second known process a mixed effluent stream comprising unreacted synthesis gas together with carbon dioxide is separated from the dimethyl ether product. However, carbon dioxide is then subsequently separated from the synthesis gas. This can be done by washing this stream with for instance a suitable amine compound such as methyl di-ethanol amine, MDEA. The synthesis gas stream, which is free of carbon dioxide, is then recycled to the synthesis gas process stream entering the reactor. The carbon dioxide obtained may be employed in other processes for instance in the preparation of synthesis gas from natural gas by auto-thermal carbon dioxide reforming.

In the third known process only synthesis gas is separated from the dimethyl ether product and carbon dioxide. The dimethyl ether product thus contains both methanol and carbon dioxide. The separated synthesis gas is recycled to the synthesis gas process stream entering the reactor.

Various solvents are known in the prior art for removing carbon dioxide from mixtures with synthesis gas. The choice of solvent is dependent on the ability to dissolve dimethyl ether and carbon dioxide and the ideal solvent should have a high solubility for carbon dioxide and a low volatility.

U.S. Pat. No. 5,908,963 discloses a process for the preparation of dimethyl ether from synthesis gas, in which synthesis gas is separated from dimethyl ether product, and recycled to the synthesis gas process stream entering the dimethyl ether synthesis loop. The presence of excess methanol in the dimethyl ether product is the focus of the disclosed process and the removal of carbon dioxide is not addressed.

U.S. Pat. No. 6,458,856 discloses a one-step catalytic conversion process for dimethyl ether preparation. After catalytic conversion of synthesis gas to dimethyl ether the effluent from the reactor is separated into a vapour mixture comprising dimethyl ether, carbon dioxide and unconverted synthesis gas. The vapour mixture is scrubbed using a scrubbing solvent to remove dimethyl ether and carbon dioxide from unconverted synthesis gas. The scrubbing solvent comprises a mixture of dimethyl ether and methanol. The unconverted synthesis gas is recycled to the dimethyl reactor.

This reference also discloses prior art in which scrubbing solvents such as methanol, water, methanol/water mixtures, dimethyl ether or ethanol are used.

Dimethyl ether is a good solvent for carbon dioxide, but is very volatile, whereas methanol is a poorer solvent for carbon dioxide than dimethyl ether but has the advantage of being less volatile. A process for preparing dimethyl ether from synthesis gas which makes use of a solvent having high solubility for carbon dioxide and simultaneously low volatility is therefore desirable.

SUMMARY OF THE INVENTION

In its general aspect, the invention preparation of pure dimethyl ether by removal of carbon dioxide and other impurities being present in the product from the ether synthesis by means of a physical wash.

More specific, the invention is a process for the preparation of dimethyl ether product by catalytic conversion of synthesis gas to dimethyl ether comprising the steps of contacting a stream of synthesis gas comprising carbon dioxide in a dimethyl ether synthesis step in one or more reactors and with one or more catalysts being active in formation of methanol and dehydration of methanol to dimethyl ether, to form a product mixture comprising the dimethyl ether and carbon dioxide, washing the product mixture in a scrubbing zone with a liquid solvent being rich in dialkyl ether of a polyalkylene glycol and thereby dissolving carbon dioxide and dimethyl ether in the liquid solvent, treating the liquid solvent being withdrawn from the scrubbing zone sequentially in separation zone to effect desorption of the dissolved carbon dioxide and to recover a substantially pure dimethyl ether product and the liquid solvent in its substantially lean form and recycling the lean liquid solvent to the scrubbing zone.

Liquid solvents being particularly suitable for use in the invention is a mixture of dimethyl ethers of polyethylene glycol and has a formula of $CH_3(CH_2CH_2O)nCH_3$, where n is a number between 2 and 10.

These dialkyl ether polyglocols are known to effectively dissolve hydrogen sulphide and carbon dioxide contained in e.g. natural gas and conventionally employed in the Selexol© process.

In further an embodiment, hydrogen and carbon monoxide unconverted synthesis gas further contained in the product mixture being separated from the dimethyl ether product and carbon dioxide is recycled to the dimethyl ether synthesis.

In yet another embodiment of the invention each separation zones comprise one or more flash separators for the desorption of captured carbon dioxide and dimethyl ether.

The product mixture from the ether synthesis step may additionally contain small amounts of methanol and water. These compounds may be separated from the product mixture either upstream the scrubbing zone by means of cooling and condensation or within the scrubbing zone by absorption in the liquid solvent. In any way, the product mixture being withdrawn from the synthesis step has to be cooled to a temperature of between 0 and 80° C. before being introduced into the scrubbing zone.

In the scrubbing zone the product mixture is contacted with the liquid solvent at elevated pressure in the range of 20 to 100 bar at a temperature of the solvent of between −10 and 40° C. at the inlet of scrubbing zone.

At the above conditions in the scrubbing zone, minor amounts of hydrogen and carbon monoxide from unconverted synthesis gas further contained in the product mixture will pass through the scrubbing zone without being dissolved in the liquid solvent.

Thus, in further an embodiment of the invention hydrogen and carbon monoxide being withdrawn from the scrubbing zone are recycled to the ether synthesis step for further conversion to dimethyl ether.

A further embodiment of the invention is a process for the preparation of dimethyl ether product by catalytic conversion of synthesis gas to dimethyl ether comprising the steps of contacting a stream of synthesis gas comprising carbon dioxide in a dimethyl ether synthesis step in one or more reactors and with one or more catalysts being active in formation of methanol and dehydration of methanol to dimethyl ether to form a product mixture comprising dimethyl ether, methanol and carbon dioxide, washing the product mixture in a scrubbing zone with a liquid solvent being rich in dialkyl ether of a polyalkylene glycol and thereby dissolving carbon dioxide, methanol and dimethyl ether in the liquid solvent, treating the liquid solvent being withdrawn from the scrubbing zone in a separation zone to effect desorption of the dissolved carbon dioxide, methanol and recovering a substantially pure dimethyl ether product from zone and a lean liquid solvent from the third separation zone and recycling the lean liquid solvent to the scrubbing zone.

BRIEF DESCRIPTION OF THE DRAWINGS

FIG. 1 shows a simplified flow sheet of a specific embodiment of the invention utilising an ether product mixture purification scheme with a methanol condensation step upstream a scrubbing zone a liquid solvent of a dialkyl ether of a polyalkylene glycol.

DETAILED DESCRIPTION OF THE INVENTION

FIG. 1 shows the general process steps in purification of dimethyl ether in accordance with a specific embodiment of the invention.

Synthesis gas 1 is sent to DME synthesis reactor 2 for catalytic conversion to methanol and DME according to reactions (1) and (2). The shift reaction also takes place according to reaction (3). The effluent from DME synthesis reactor 2 contains product mixture 3, which comprises a mixture of dimethyl ether, carbon dioxide and unconverted synthesis gas together with minor amounts of methanol and water. Product mixture 3 is cooled in cooler 4 and passed to separation unit 5, for the condensation of the amounts of methanol and water in cooled gas 3. The condensed methanol and water are separated from the remaining product gas through line 6. Remaining product mixture 7 is passed to scrubber unit 8. The amounts of carbon dioxide and dimethyl ether contained in the product mixture being introduced into unit 8 are dissolved in a lean cooled liquid solvent, which is introduced at top of unit 8 through line 16.

Unconverted synthesis gas being further contained in the product mixture and not being dissolved in the solvent leaves unit 8 through line 9 is recycled to synthesis gas stream 1.

Liquid solvent 10 containing dissolved carbon dioxide and dimethyl ether is withdrawn from unit 8 and is introduced into desorber 14 for the selective desorption of the amount of carbon dioxide 12 and the recovery of substantially pure dimethyl ether 15.

Lean liquid solvent being withdrawn from desorber 14 is recycled in line 16 to scrubber unit 8. Prior to introduction into the scrubber, the solvent is cooled in cooler 18.

The above described process flow scheme is simplified and some additional process steps may be carried out. As an example may the separation of methanol and water in separation unit 5 be enhanced by means of dimethyl ether being dissolved in liquid solvent 10 and being introduced in a split stream from stream 10 into unit 5.

If a propellant grade dimethyl ether product is required, product 15 may be passed through a fixed bed with a carbon dioxide adsorbent (not shown) for the deep purification of the dimethyl ether product.

Suitable carbon dioxide adsorbents for use in this embodiment of the invention are selected from group of zeolites and molecular sieves, such as 13-X and activated alumina.

The invention claimed is:

1. Process for the preparation of dimethyl ether product by catalytic conversion of synthesis gas to dimethyl ether comprising the steps of:
    contacting a stream of synthesis gas comprising carbon dioxide in a dimethyl ether synthesis step in one or more reactors and with one or more catalysts being active in formation of methanol and dehydration of methanol to dimethyl ether, to form a product mixture comprising the dimethyl ether and carbon dioxide;
    washing the product mixture in a scrubbing zone with a liquid solvent being rich in dialkyl ether of a polyalkylene glycol and thereby dissolving carbon dioxide and dimethyl ether in the liquid solvent;
    treating the liquid solvent being withdrawn from the scrubbing zone sequentially in separation zone to effect desorption of the dissolved carbon dioxide and to recover a substantially pure dimethyl ether product and the liquid solvent in its substantially lean form; and
    recycling the lean liquid solvent to the scrubbing zone.

2. Process of claim 1, wherein the liquid solvent is a mixture of dimethyl ethers of polyethylene glycol and has a formula of $CH_3(CH_2CH_2O)nCH_3$, where n is a number between 2 and 10.

3. Process of claim 1, wherein synthesis gas being depleted in carbon dioxide is recycled from the scrubbing zone to the dimethyl ether synthesis step.

4. Process of claim 1, wherein the separation zones comprise a series of flash separators.

5. Process according to claim 1, wherein the product mixture from the ether synthesis step further comprises methanol, and wherein the methanol is separated from the product mixture in a separation step upstream the scrubbing zone.

6. Process according to claim 1, wherein the substantially pure dimethyl ether product is subjected to a carbon dioxide adsorption step in a fixed bed of a carbon dioxide adsorbent.

7. Process for the preparation of dimethyl ether product by catalytic conversion of synthesis gas to dimethyl ether comprising the steps of:

contacting a stream of synthesis gas comprising carbon dioxide in a dimethyl ether synthesis step in one or more reactors and with one or more catalysts being active in formation of methanol and dehydration of methanol to dimethyl ether to form a product mixture comprising dimethyl ether, methanol and carbon dioxide;

washing the product mixture in a scrubbing zone with a liquid solvent being rich in dialkyl ether of a polyalkylene glycol and thereby dissolving carbon dioxide methanol and dimethyl ether in the liquid solvent;

treating the liquid solvent being withdrawn from the scrubbing zone in a separation zone to effect desorption of the dissolved carbon dioxide, methanol and recovering a substantially pure dimethyl ether product from zone and a lean liquid solvent from the third separation zone;

and recycling the lean liquid solvent to the scrubbing zone.

8. Process according to claim 7, wherein the substantially pure dimethyl ether product is subjected to a carbon dioxide adsorption step in a fixed bed of a carbon dioxide adsorbent.

\* \* \* \* \*